United States Patent [19]

Itoi

[11] Patent Number: 5,671,748
[45] Date of Patent: Sep. 30, 1997

[54] ULTRASOUND ENDOSCOPE HAVING ULTRASOUND PROBE IN COMBINATION WITH ENDOSCOPIC OBSERVATION SYSTEM

[75] Inventor: Hiromu Itoi, Omiya, Japan

[73] Assignee: Fuji Photo Optical Co., Ltd., Omiya, Japan

[21] Appl. No.: 636,966

[22] Filed: Apr. 24, 1996

[30] Foreign Application Priority Data

Apr. 28, 1995 [JP] Japan .................................. 7-127424

[51] Int. Cl.$^6$ .................................................. A61B 8/12
[52] U.S. Cl. .............................. 128/662.06; 600/117
[58] Field of Search ........................ 128/660.09, 660.1, 128/662.03, 662.06; 600/117

[56] References Cited

U.S. PATENT DOCUMENTS

| | | | |
|---|---|---|---|
| 4,880,011 | 11/1989 | Imade et al. | 128/662.06 |
| 5,099,850 | 3/1992 | Matsui et al. | 128/662.06 |

*Primary Examiner*—Francis Jaworski
*Attorney, Agent, or Firm*—Oblon, Spivak, McClelland, Maier & Neustadt, P.C.

[57] ABSTRACT

An ultrasound endoscope employing a radial scan type ultrasound probe in combination with an endoscope having a rotatable fore section on a front part of an endoscopic insertion rod for turning a view field of endoscopic observation images by the so-called twist operation. The ultrasound probe is provided with an angle detection means and an image rotating means thereby to turn ultrasound images on display on a monitor screen into a direction which matches endoscopic observation images at the time of twist operations.

3 Claims, 7 Drawing Sheets

ULTRASOUND ENDOSCOPE HAVING ULTRASOUND PROBE IN COMBINATION WITH ENDOSCOPIC OBSERVATION SYSTEM

BACKGROUND OF THE INVENTION

1. Field of the Art

This invention relates to an ultrasound endoscope having an ultrasound probe in combination with an endoscopic observation system, and more particularly to an ultrasound endoscope incorporating a radial scan type ultrasound probe in combination with an endoscope capable of the so-called twist operation, i.e., an operation of turning a fore end portion of a catheter-like endoscopic insertion rod about its axis for the purpose of turning a view field of endoscopic observation images, the ultrasound probe having means for turning the view field of ultrasound observation images through an angle commensurate with a twist angle of the endoscopic insertion rod to prevent directional divergence of ultrasound images on display on a monitor screen from endoscopic observation images.

2. Prior Art

In addition to or in combination with endoscopic observation systems, ultrasound probes are widely resorted to in medical examinations for the purpose of obtaining ultrasound images of tomographic sections through tissues of intracavitary walls or internal organs of particular interest. The ultrasound endoscopes which are used on such occasions normally have an ultrasound scanning mechanism of an ultrasound observation system integrally assembled into a catheter-like endoscopic insertion rod to be introduced into an internal cavity or canal of a patient. In some cases, a separate ultrasound probe of a small diameter is inserted into an intracavitary region of interest by way of a biopsy channel which is provided internally of an endoscopic insertion rod mainly for insertion of forceps or other bioptic instruments. In this connection, it is to be understood that the terms "endoscopic ultrasound observation system" and "ultrasound endoscope" which may appear in the following description both include an ultrasound probe which is integrally incorporated into an endoscopic observation system as well as an ultrasound probe which is designed to be removably fitted in a biopsy channel of an endoscope as mentioned above.

As well known in the art, the endoscopic observation systems on ultrasound probes are usually provided for observation of optical surface-wise images of intracavitary portions of interest. In case of an optical endoscope, images of intracavitary portions under observation are optically produced at an eyepiece at the end of an image guide, while in case of an electronic endoscope images are picked up by a solid-state image sensor element and displayed on a viewing screen of a monitor. On the other hand, ultrasound probes are employed for the purpose of obtaining information in certain tomographic sectional areas of intracorporeal tissue layers, and can be classified into an electronic scan type employing a large number of ultrasound transducer elements which are sequentially activated by an electronic drive to cover a predetermined scanning range and a mechanical scan type employing an ultrasound transducer element which is mechanically driven over a certain scanning range. Further, the ultrasound transducer element or elements can be operated in different scan modes, i.e., a linear scan mode for obtaining tomographic ultrasound images in a linear direction and a radial scan mode for tomographic ultrasound images in radial directions.

With regard to the radial scan mode, most of ultrasound probes of this sort are capable of making scans continuously over a full range of 360° no matter whether they are of the electronic scan type or mechanical scan type, resulting in a tomographic ultrasound image which has no directionability in particular by itself. However, in order to display ultrasound images on a monitor screen, ultrasound image signals obtained by a radial scanning operation are divided into frames which each contain an ultrasound image in a view field of 360°, and displayed frame by frame on the monitor screen in reference to a predetermined original scanning position. In so doing, it is desirable to display ultrasound images in a manner which matches endoscopic observation images in viewing direction as well as in angular scanning position. This is a matter of utmost importance not only in a case where endoscopic observation images picked up by an electronic endoscope are also displayed on a monitor screen as mentioned above, but also in the case of an optical endoscope where the operator should be able to view ultrasound images in the same direction as the optical endoscopic observation images viewed through a light guide and an eyepiece mounted on a manipulating head assembly of the endoscope, particularly with regard to the positions of upper and lower sides and right and left sides of images on display. This is because divergence or discrepancies between ultrasound observation images and endoscopic observation images in the rotational direction could make it difficult for the operator to spot an exact position of a diseased portion or to give an appropriate diagnosis on an intracorporeal portion under examination.

Of course, ultrasound endoscopes in which an ultrasound observation system is integrally assembled into an endoscopic insertion rod are capable of adjusting the position of an ultrasound transducer element such that, when stopped, it is located at a predetermined angular position within a view field of endoscopic observation, which coincides with the afore-mentioned original scanning position on the monitor screen for both of the ultrasound and endoscopic observation images. In case of an ultrasound probe of the type which is designed to be inserted through a biopsy channel of an endoscope, it is the usual practice to bring the view field of ultrasound observation images into agreement with that of the endoscopic observation images either simply by adjusting the angular position of an ultrasound transducer after placing the ultrasound probe in position within a biopsy channel of the endoscope or by turning an ultrasound transducer element into a predetermined angular position which corresponds to an original scanning position for both of ultrasound and endoscopic observation images. With a measure of this sort, one can grip the exact position, depth and shape of a diseased portion by analyzing ultrasound images in relation with endoscopic images.

In a wide intracavitary space, a broader endoscopic view filed can be secured quite easily by bending a fore end section of the endoscopic insertion rod and turning the bent fore end section through a certain angle. The operation of turning an endoscopic insertion rod about its axis, which is generally referred to as "a twist operation", has been feasible with certain types of specula or the like. In order to enable such twist operations for an endoscope, the endoscopic insertion rod is divided into two relatively rotatable rod sections, namely, a non-rotatable rear rod section which is fixedly connected to a manipulating head assembly of the endoscope and a rotatable fore rod section which is rotatably connected to the fore end of the non-rotatable rear rod section. In such a case, some component parts of the endoscopic imaging system, such as illumination and observation windows, are formed in part of the rotatable fore rod section, while elongated component parts such as fiber optics bundle and signal cable are passed coextensively through the rotatable and non-rotatable rod sections. If the movable fore rod section is turned by a twist operation, naturally the elongated component parts are subjected to a torsional force. However, since these coextensively fitted components are formed of a material with a sufficient degree of flexibility for preventing deformations, breakage or damages as would otherwise caused by torsional forces expected to be applied in twist operations. Although there is a limit to the rotational angle of the rotatable section of the endoscopic insertion rod, a rotation through 270°, that is, a three-quarter rotation would be sufficient to capture almost the entire surroundings of an intracavitary region within the view field of the endoscopic observation system without exerting objectionably large torsional forces to the elongated component parts which are fitted in the insertion rod.

In connection with endoscopic insertion rods which are capable of twist operations as mentioned above, and particularly in connection with endoscopes incorporating a radial scan ultrasound transducer of an ultrasound scanning mechanism, there has been a problem that the view field of ultrasound images is turned away from that of endoscopic observation images in the course of a twist operation. More specifically, by a twist operation through 180°, for example, the observation window of the endoscopic imaging system, at the distal end of the endoscopic insertion rod, is turned upside down and at the same time its right and left sides are reversed relative to the eyepiece fixed on the manipulating head assembly of the endoscope. On the other hand, the radial scan ultrasound transducer element at the fore end of a rotational drive transmission means which is rotatably fitted in the rotatable section of the endoscopic insertion rod, for example, a rotation transmission means which is connected to an electric motor or other rotational drive means of an ultrasound scanning mechanism, for rotations independently of the rotatable section of the insertion rod. Therefore, at the time of a twist operation, the rotational transmission means of the ultrasound transducer would not follow the rotation of the rotatable section of the endoscopic insertion rod despite the trouble that ultrasound images on display on a monitor screen are directionally diverged from endoscopic observation images until they are completely reversed relative to the latter in vertical and lateral directions.

SUMMARY OF THE INVENTION

In an attempt to overcome the above-described problem or drawback with conventional ultrasound probes in combined endoscopic and ultrasound observation systems, it is an object of the present invention to provide an ultrasound endoscope which is capable of turning the view field of ultrasound observation images on display on a monitor screen in the same direction as that of endoscopic observation images when a rotatable section of an endoscopic insertion rod is turned about it axis at the time of a twist operation, thereby preventing divergence in the rotational direction of the view field of ultrasound observation images from that of endoscopic observation images.

In accordance with the present invention, the above-stated objective is achieved by the provision of an ultrasound endoscope employing a radial scan type ultrasound probe in combination with an endoscope having a rotatable fore section on a front part of an endoscopic insertion rod, the ultrasound probe including an angle detection means for detecting a rotational angle of the rotatable fore section of the endoscopic insertion rod when operated to turn a view field of endoscopic observation images of the endoscope; and an ultrasound image rotating means for turning a view field of ultrasound observation images of the ultrasound probe through an angle commensurate with the rotational angle of the rotatable fore section of the endoscopic insertion rod on the basis of a signal from the angle detection means.

As the rotatable fore section of the endoscopic insertion rod is turned about its axis relative to a fixed rod section for a twist operation, the view field of the endoscopic observation image is turned around accordingly. The rotational angle of the rotatable rod section is detected by the angle detection means to produce a detection signal, according to which ultrasound images on display on a monitor screen are turned around through a corresponding angle by the ultrasound image rotating means. Therefore, in a twist operation, ultrasound observation images are rotated exactly in the same directions as endoscopic observation images to preclude directional divergences between the endoscopic and ultrasound observation images. Accordingly, the position, depth and shape of a diseased portion which has been spotted in an tomographic ultrasound image can be easily ascertained concurrently on an endoscopic observation image, making it possible to improve the accuracy of ultrasound examinations or diagnosis to a significant degree.

The above and other objects, features and advantages of the invention will become apparent from the following description, taken in conjunction with the accompanying drawings which show by way of example preferred embodiments of the invention.

DESCRIPTION OF PREFERRED EMBODIMENTS

Hereafter, the present invention is described more particularly by way of its preferred embodiments with reference to the accompanying drawings. Shown in FIGS. 1 through 6 is a first embodiment of the invention, employing an ultrasound probe 1 which is extractably fitted in an endoscopic insertion rod 20 as seen particularly in FIG. 2. Although in this case arrangements are made to view endoscopic observation images through an eyepiece which is provided on a manipulating head assembly of the endoscope, the endoscope may be of the electronic type employing a solid-state image sensor element such as CCD or the like.

Figure 2:
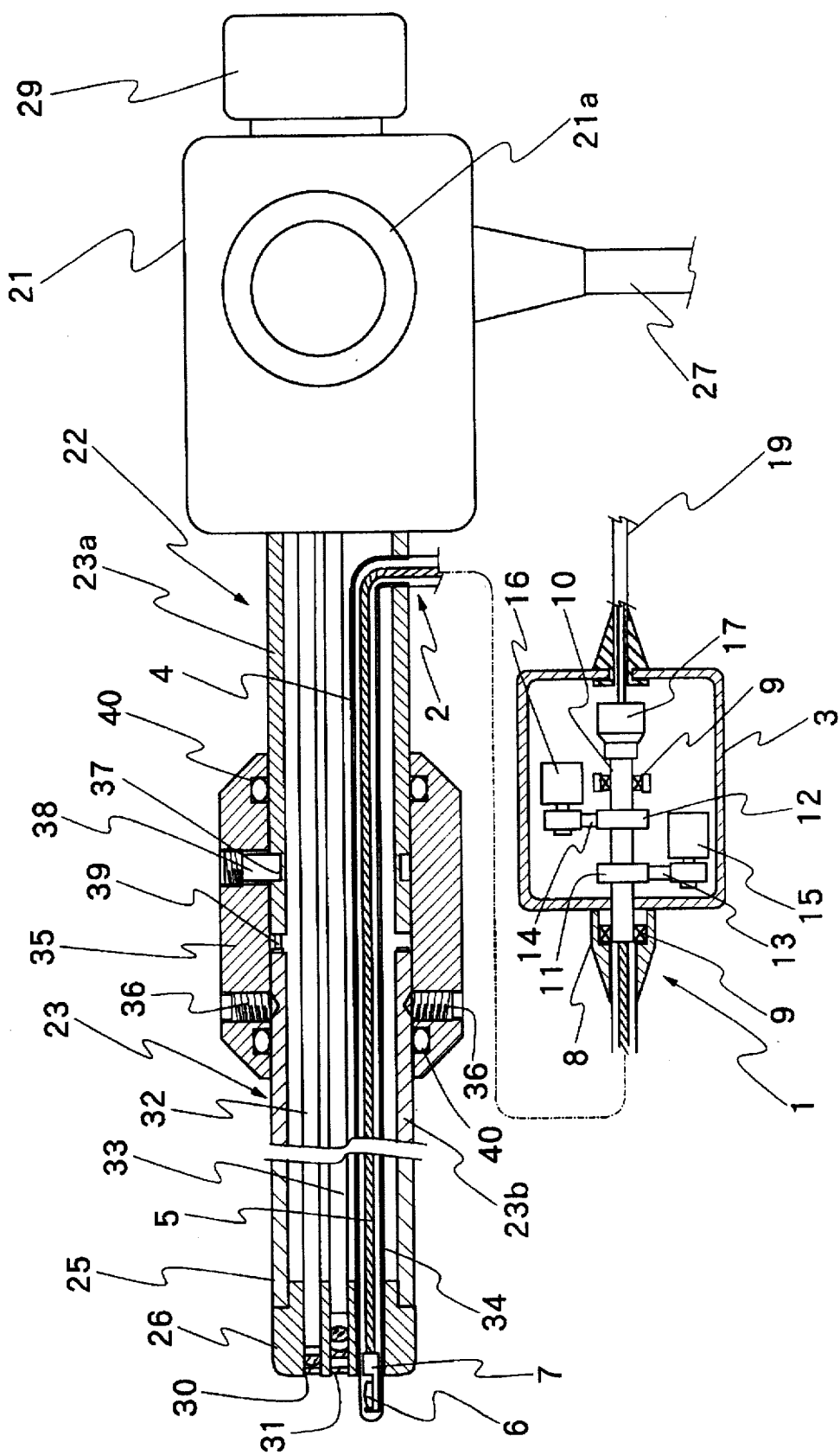
FIG. 2 is a schematic sectional view of an endoscopic insertion rod employed in the embodiment of FIG. 1.

As seen in FIG. 2, the ultrasound probe 1 is largely constituted by a catheter member 2 and a radial scan drive 3. The catheter member 2 is provided with a flexible tube 4 encasing a flexible rotation transmission shaft 5 which consists of a tightly wound metal wire coil or coils. Connected to the fore end of the flexible shaft 5 is a cradle plate 7 which fixedly supports thereon an ultrasound transducer element 6. The flexible shaft 5 is extended between the cradle plate 7 and the radial scan drive 3 through a connector 8 which is provided at the rear proximal end of the catheter member 2.

A rotational drive shaft 10 which is rotatably mounted on the radial drive 3 through bearings 9 is provided with a pair of pulleys 11 and 12. The drive shaft 10 is coupled with a motor 15 and an encoder 16 through transmission belts 13 and 14 which are lapped around the pulleys 11 and 12, respectively. Upon actuating the motor 15 to rotate the drive shaft 10, its rotation is transmitted through the flexible shaft 5 to the ultrasound transducer element 6 at the fore end of the flexible shaft 5 to rotate same about the longitudinal axis of the catheter member 2. The rotation of the ultrasound transducer element 6 is constantly picked up by the encoder 16. In a radial ultrasound scan, on the basis of signals from the encoder 16, an ultrasound signal is shot into intracorporeal regions of interest at predetermined angular intervals during rotation of the ultrasound transducer element 6, followed by reception of return echo signals, for example, from tomographic sections of intramural tissues.

Connected to the ultrasound transducer element 6 is a signal cable which is passed internally of the flexible transmission shaft 5 and connected to electrodes (not shown) provided within the drive shaft 10. A rotary connector 17 is coupled with the drive shaft 10 to permit relative rotations between the rotatable signal cable which is connected to the ultrasound transducer element 6 for rotation therewith and a non-rotatable signal cable running through a cable 19 which is disconnectibly connected to a signal processor 18a on an ultrasound image observation terminal 18 having a monitor screen 18b along with the signal processor 18a.

Figure 1:
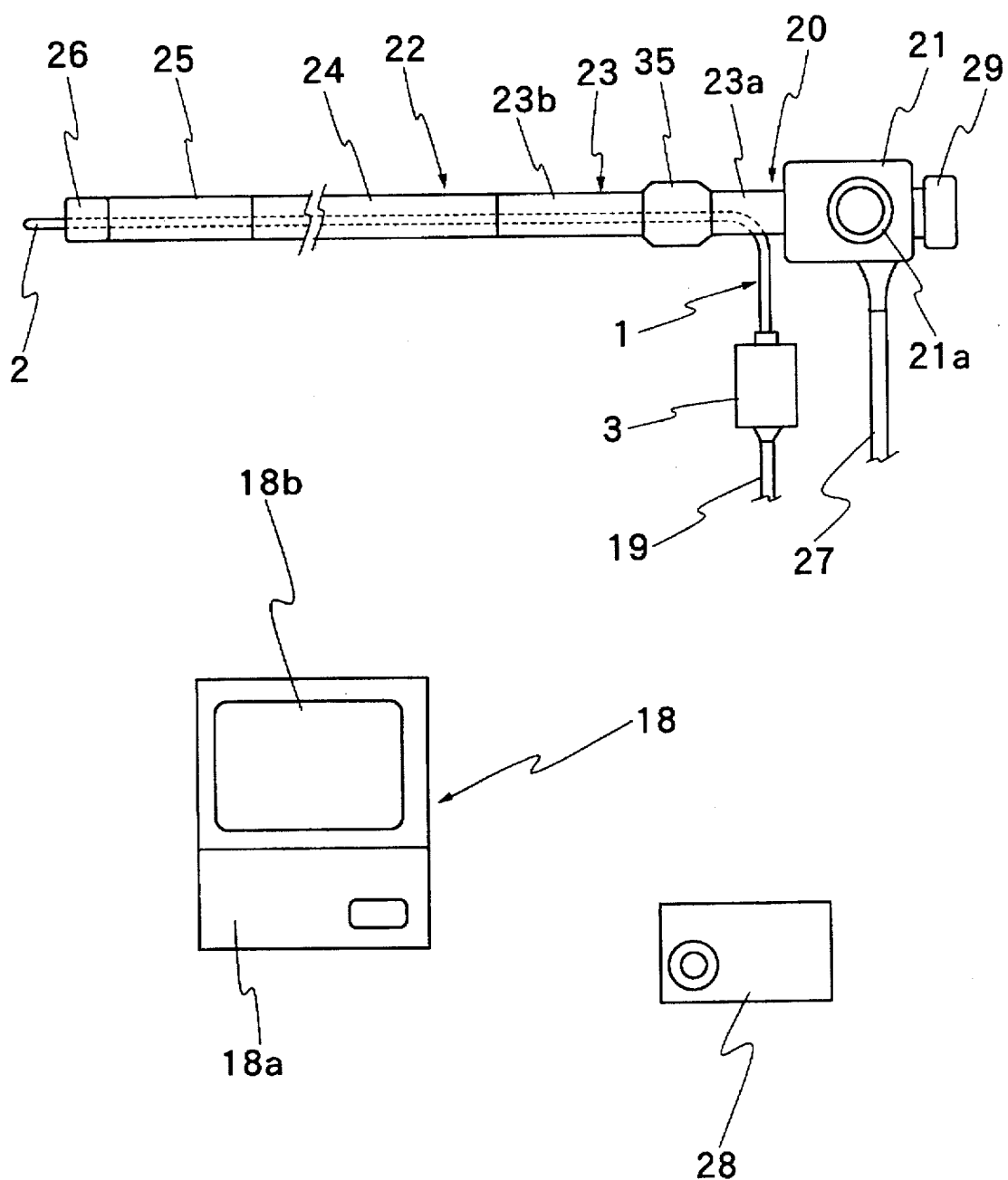
FIG. 1 schematically shows the general layout of an endoscopic ultrasound examination system embodying the present invention.

On the other hand, the endoscope 20 includes a manipulating head assembly 21 and an insertion rod 22 which is extended forward from the manipulating head assembly 21 for introduction into an intracavitary region to be examined. As shown in FIG. 1, the endoscopic insertion rod 22 is mostly constituted by a freely bendable, flexible rod section 24, except a rigid rear section 23 which is provided over a predetermined length at its rear or proximal end connected to the manipulating head assembly 21, an angle section 25 which is connected to the fore end of the flexible section 24 and bendable in an arbitrary direction by manipulation of an angle knob 21a on the manipulating head assembly 21, and a rigid tip end section 26 which is connected to the fore end of the angle section 25. Extended out on the rear side of the head assembly 21 is a flexible light guide 27 which is disconnectibly connected to a light source 28 at its proximal end. Further, for observation of images picked up by the endoscope itself, an eyepiece 29 is connected to the manipulating head assembly 21 on its rear side or on the side away from the insertion rod 22.

Opened in the rigid tip end section 22 at the distal end of the insertion rod 22 are an illumination window 30 and an observation window 31 of the endoscopic imaging system.

The illumination window 30 and observation window 31 are fitted with an illumination lens and an objective lens, respectively. Disposed face to face with the illumination window 30 is a light emitting end of the light guide 32 in the form of a bundle of fiber optics, which is extended through the flexible light guide cable 27 via the manipulating head assembly 21 and connected to the light source 28. Located at the focus of the objective lens of the endoscopic observation window 31 is an image input end of an image guide 33 which has the other image output end extended as far as and disposed face to face with the eyepiece 29 on the manipulating head assembly 21.

In addition to the above-described components which are coextensively fitted in the insertion rod 22, a biopsy channel 34 is provided for insertion of forceps or other instruments including the catheter member 2 of the ultrasound probe 1. More specifically, in order to make ultrasound scans, the catheter member 2 is inserted into an internal cavity or canal of a patient through the biopsy channel 34 of the endoscopic insertion rod 22 in such a way that a fore end portion of the catheter member 2 is protruded from the fore end of the insertion rod 22 by a predetermined extension length.

The rigid rod section 23 which connects the endoscopic insertion rod 22 to the manipulating head assembly 21 includes a cylindrical stationary rear shell 23a which is fixedly connected to the head assembly 21, and a similarly cylindrical movable front shell 23b which is rotatable about its axis relative to the stationary rear shell 23a. On the other hand, the flexible rod section 24, angle section 25 and rigid tip end section 26 of the insertion rod 26 are not rotatable relative to the movable front shell 23b. As a consequence, when the movable front shell 23b is turned about its axis, the insertion rod sections forward of the rear rigid section 23, that is to say, the flexible rod section 24, angle section 25 and rigid tip end section 26 are turned with the front shell 23b to permit the afore-mentioned twist operations.

Further, in order to permit twist operations, a twist ring 35 is fitted on and across confronting ends of the rear and front shells 23a and 23b. This twist ring 35 is securely fixed to the movable front shell 23b by means of set screws 36, so that, upon turning the twist ring 35, the movable front shell 23b is caused to turn together with the ring 35. For the purpose of delimiting the rotational angle of the twist ring 35, an arcuate groove 37 is provided on the circumference of the fixed rear shell 32a through a predetermined angle, for example, through 270°, and engaged with a positioning pin 38 which is planted on the inner periphery of the twist ring 35.

Figure 3:
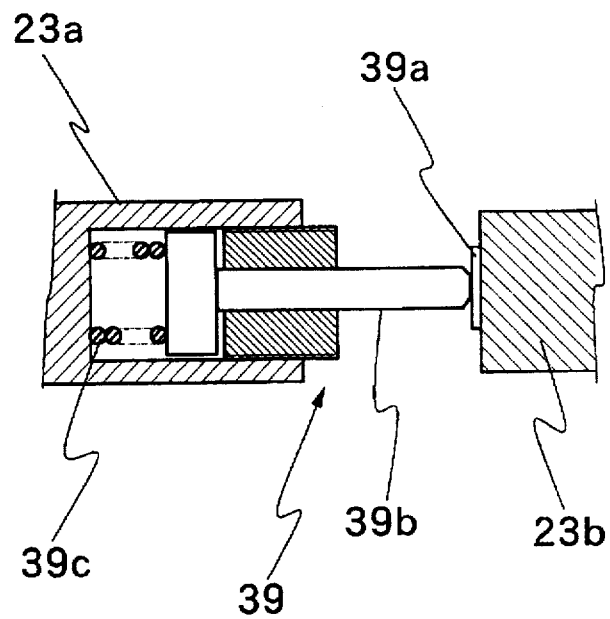
FIG. 3 is a fragmentary sectional view of a potentiometer electrode.
Figure 4:
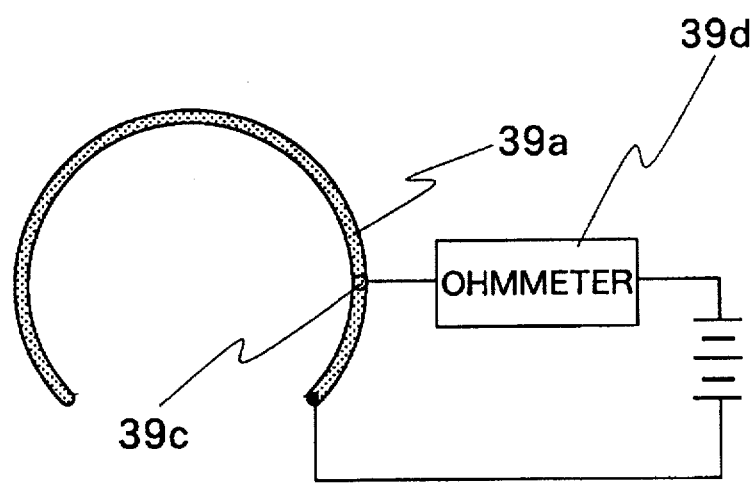
FIG. 4 is a diagrammatic illustration explanatory of a potentiometer circuit arrangement.

Further, as shown in FIGS. 3 and 4, the movable front shell 23b is positioned to confront the rear stationary shell 23a at a predetermined space therefrom for the purpose of detecting a rotational angle of the movable front shell 23b relative to the rear shell 23a. More particularly, a resistor 39a of an arcuate shape is provided on the confronting end face of the front movable shell 23b through a predetermined angle, for example, through 270°. On the other hand, an electrode pin 39b is projected from the rear stationary shell 23a and urged into resilient sliding contact with the resistor 39a by means of a spring 39c. Accordingly, the resistance value varies as the electrode pin 39b is slid on and along the resistor 39a. The resistor 39a and electrode pin 39b constitute a potentiometer for detection of rotational angles of the movable shell 23b, together with an ohmmeter 39c which detects variations in the resistance value. Indicated at 40 is a seal ring which is interposed between the twist ring 35 and the stationary and movable shells 23a and 23b of the rear rigid section 23 of the endoscopic insertion rod 22.

With the foregoing arrangements, for an endoscopic examination, the insertion rod 22 of the endoscope 20 is introduced into an internal cavity or canal of a patient. In case there is necessity for an ultrasound scan, the catheter member 2 of the ultrasound probe 1 is inserted through the biopsy channel 34 of the endoscope 20 into an intracavitary region under examination, protruding a fore end portion of the catheter member 2 from the rigid tip end section 26 of the insertion rod 26 by a predetermined length. In this state, the motor 15 on the scanner 3 is actuated to drive the ultrasound transducer element 6 rotationally for a radial scanning operation.

In this instance, when the ultrasound transducer element is put in a radial scanning operation for an ultrasound examination concurrently with or in the course of an endoscopic examination, the view field of ultrasound observation images should not be diverged in the rotational direction from that of endoscopic observation images. In displaying radial scan ultrasound images on the monitor screen 18b, such divergences of ultrasound images on display can be cancelled by adjusting an original scanning position of ultrasound images on the monitor screen 18b. The adjustments to this effect can be made either by the use of a mechanical means, or by the use of an electronic image processing/conversion means which is capable of image rotation as will be described below.

Figure 5:
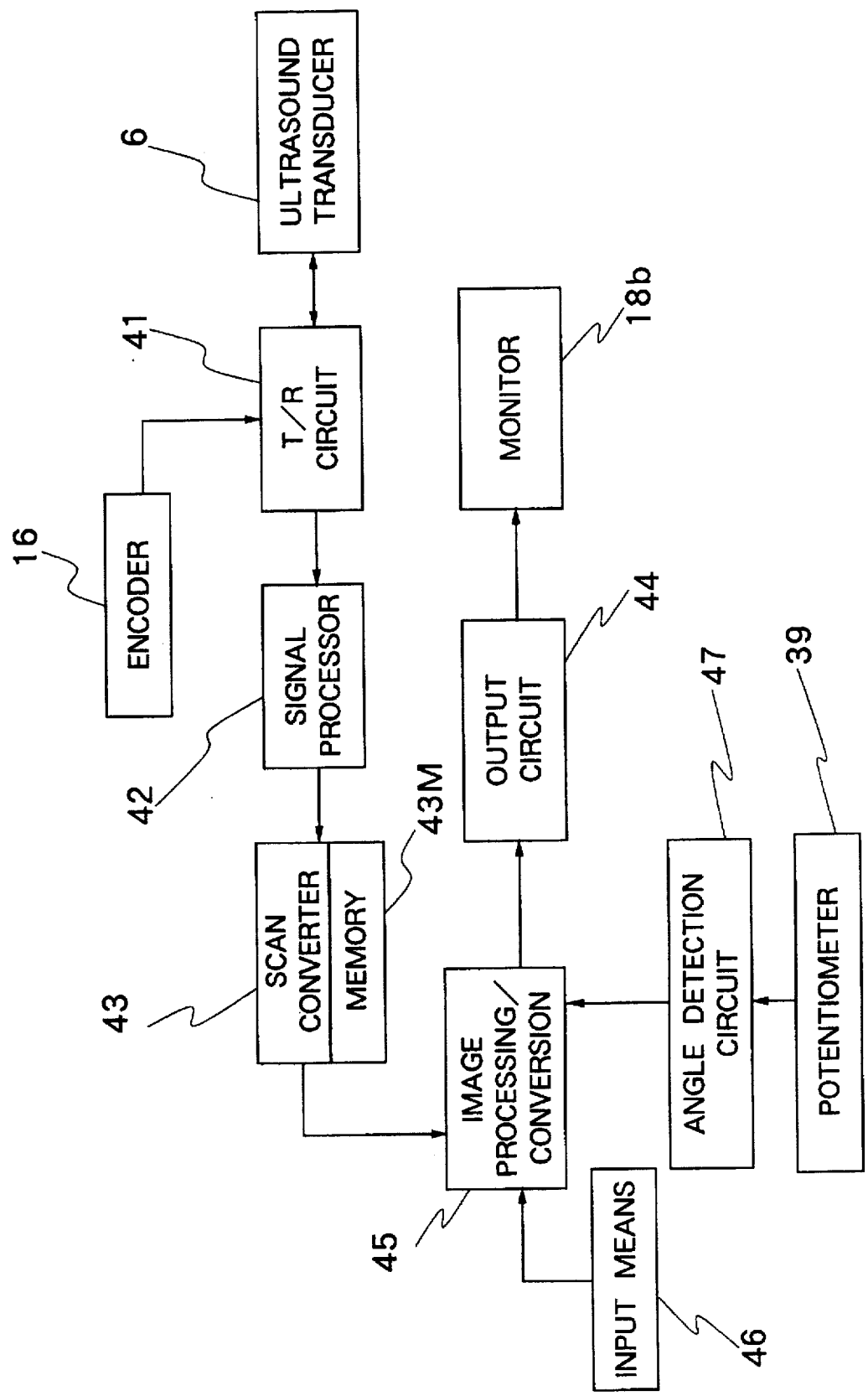
FIG. 5 is a circuit diagram of an ultrasound image processor.

Referring to FIG. 5, there is diagrammatically shown arrangements of the signal processor 18a for generating tomographic ultrasound images on the basis of received return echoes. In this figure, indicated at 41 is an ultrasound signal transmission/reception circuit which is arranged to supply a transmission trigger signal to the ultrasound transducer element 6 at predetermined angular intervals during rotation of the latter on the basis of signals from the encoder 16 to send forth an ultrasound pulse signal into intracavitary regions under observation. Upon finishing transmission of an ultrasound signal, the operation of the transmission/reception circuit 41 is switched from a transmission phase to a reception phase to receive return echo signals from a scanned section of intramural tissues through the ultrasound transducer element 6. The ultrasound return echo signals which have been received in this manner are fed to a signal processing circuit 42 to undergo amplification and other signal processing operations, and resulting ultrasound image signals are fed to memory 43M of a scan converter 43. Normally, ultrasound image signals are sent forward frame by frame from the memory 43M of the scan converter 43 to the monitor 18b through an output circuit 14. However, in this instance, output signals of the scan converter 43 are sent forward via an image processing/conversion circuit 45 which has a function of image rotation. Normally, a radial scan tomographic ultrasound image is made up of a number of acoustic lines diverging in radial directions from a center of scanning, and one of these acoustic lines is located at the initial scanning position on the viewing screen on the monitor. Therefore, ultrasound images on display on the monitor screen can be rotated by inputting a command of shifting the original scanning position in the rotational direction to the image processing/conversion circuit 45. By so doing, the view field of ultrasound images can be shifted in the rotational direction and into a position which matches the view field of endoscopic observation images.

On the other hand, the view field of endoscopic observation images as captured through the observation window 31 on the endoscopic insertion rod can be shifted into a direction of a particular target, for example, by bending the angle section 25 into a desired direction through manipulation of the angle knob. If the twist ring 35 is turned for a twist operation when the angle section 25 is in a bent state, the insertion rod sections forward of the rigid rear section 23 are turned about the axis of the insertion rod 22 to gyrate the rigid tip end section 26 around a bent joint of the angle section, turning the endoscopic view field into different directions. Accordingly, a wide endoscopic view field can be covered by bending the angle section 25 or by a twist operation as described above, without relocating the endoscopic insertion rod 22 as a whole.

In a twist operation turning the rigid tip end section 26 about its axis, the endoscopic observation window 31 at the distal end of the insertion rod is also turned around to rotate the endoscopic view field in the twisted direction. At this time, the flexible tube 4 of the catheter member 2 which is inserted in the biopsy channel 34 of the endoscopic insertion rod 22 is turned around along with the rigid tip end section 26. However, the ultrasound transducer element 6 is held in a non-rotatable state since it is connected to the drive motor 15 on the fixed side of the ultrasound probe through the flexible rotation transmission shaft 5 within the flexible tube 4 and the drive shaft 10. As a consequence, the view field of ultrasound observation is diverged from that of the endoscopic observation in the rotational direction.

Figure 6:
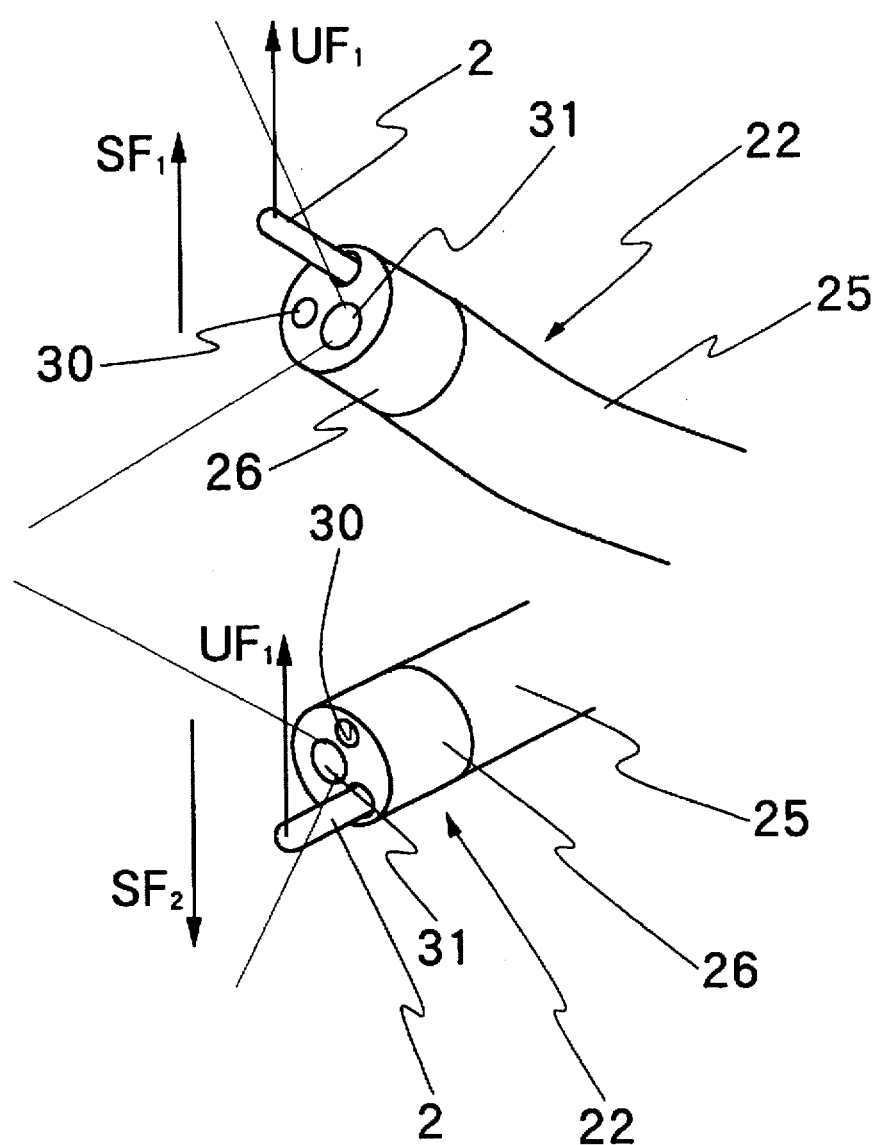
FIG. 6 is a schematic illustration explanatory of relations between a view field of ultrasound observation image and a view field of endoscopic observation image in a twist operation.

Now, when the endoscopic insertion rod 22 is not in a twisted state as indicated by solid line in FIG. 6, for example, the view field of endoscopic observation at the eyepiece 29 stands in the direction of arrow $SF_1$, and in this state the direction of ultrasound view field is adjusted as indicated by arrow $UF_1$ to show ultrasound images on the monitor screen as viewed from the same direction as the endoscopic images. Under these circumstances, if the endoscopic insertion rod 22 is turned through 180° by a twist operation, the rigid tip end section 26 of the rod is also turned through the same angle, twisting the image guide 33 by a half turn about its axis. As a result, the view filed of endoscopic observation images as viewed through the eyepiece 29 is turned upside down to stand in the direction of arrow $SF_2$. Nevertheless, the view field of ultrasound observation images remains in the same position as it was, standing in the direction of arrow $UF_1$, which is inverse to the direction of the view field of endoscopic observation images.

However, according to the invention, the rotational angle of the movable shell 23b in a twist operation is detected by the potentiometer 39 which is provided between the fixed and movable shells 23a and 23b of the rigid rear section 23, including the above-described resistor 39a and the electrode pin 39b. More specifically, output signals of the potentiometer 39 are fed to the angle detection circuit 47 to detect the rotational angle of the movable shell 23b on the basis of the resistance value of the potentiometer 39, and output signals of the angle detection circuit 47 are applied to the image processing/conversion circuit 45 for image rotation, shifting the original scanning position of ultrasound images on the monitor screen 18b in the rotational direction according to the detected rotational angle of the movable shell 23b. As a consequence, upon manipulating the twist ring 35 for a twist operation, the ultrasound images on display on the monitor screen 18b are turned into a direction which matches the direction of endoscopic observation images.

Figure 7:
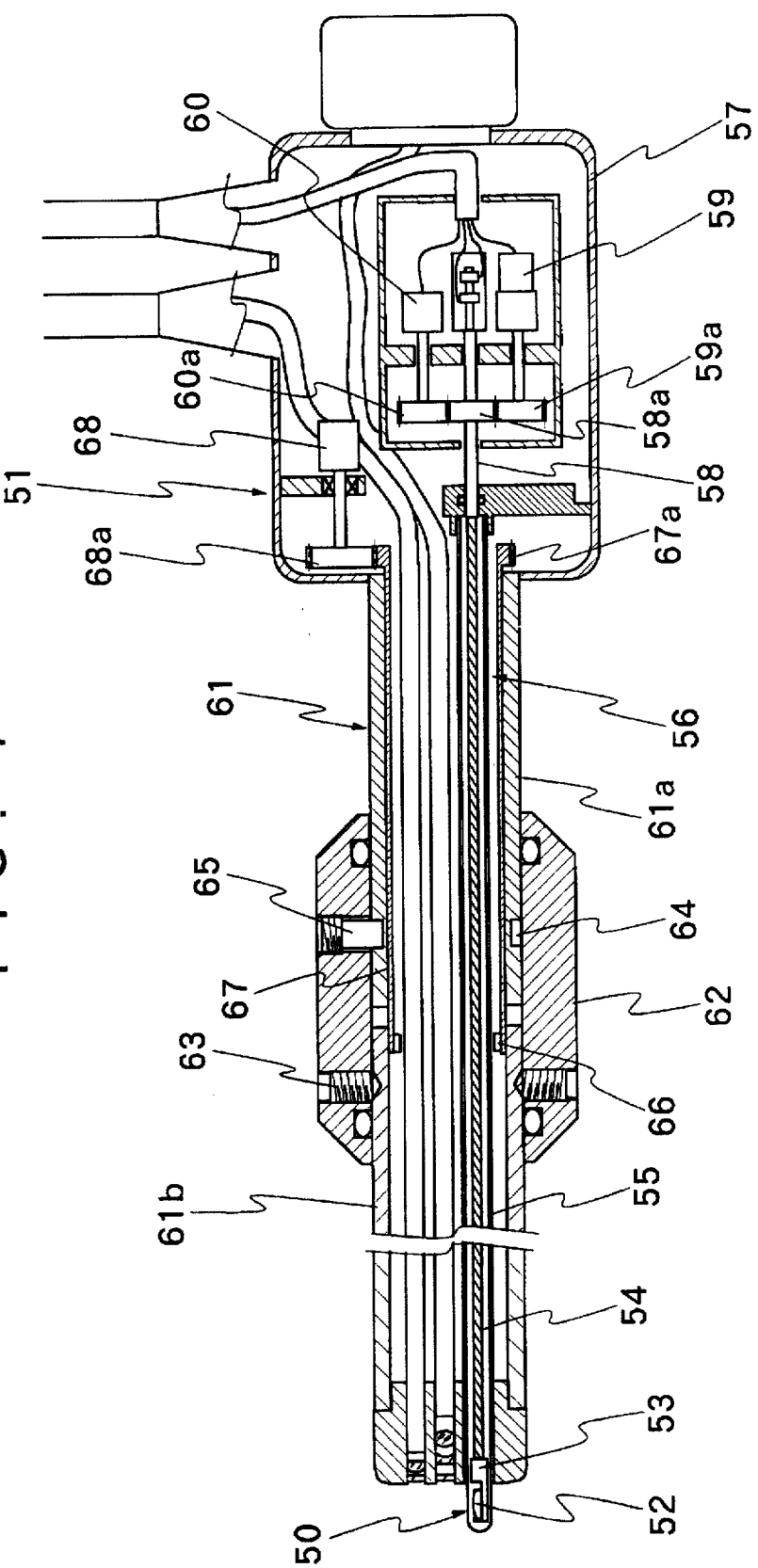
FIG. 7 is a schematic sectional view of an endoscopic insertion rod employed in a second embodiment of the invention.

Referring now to FIG. 7, there is shown a second embodiment of the invention, which has an ultrasound probe 50 of an ultrasound observation system integrally incorporated into an insertion rod of an endoscope 51. More specifically, the ultrasound probe 50 includes an ultrasound transducer element 52 mounted on a rotatable cradle plate 53 which is connected to a flexible rotation transmission shaft 54. The flexible shaft 54 is sheathed in a flexible tube 55 which is closed at its fore end and extended through the entire length of an endoscopic insertion rod 56. The rear end of the flexible shaft 54 is extended into a manipulating head assembly 57 of the endoscope, and coupled with a rotational shaft 58 within the housing of the manipulating head assembly 57. A gear 38a which is mounted on the rotational shaft 58 is meshed with a gear 59a on an output shaft of an electric motor 59 and at the same time with an input gear 60a of an encoder 60.

The endoscopic insertion rod 56 is provided with a rigid rear end section 61 over a predetermined length from its rear end which is connected to the manipulating head assembly 57. This rigid rod section 61 is constituted by a cylindrical fixed shell 61a which is fixedly connected to the manipulating head assembly 57, and a similarly cylindrical movable shell 61b which can be turned about its axis at the time of a twist operation. A twist ring 62 which is fitted on and across confronting end portions of the fixed and movable shells 61a and 61b is securely fixed to the movable shell 61a by means of set screws 63 to turn the latter therewith when the twist ring 62 is turned by the operator. On the other hand, in a manner similar to the foregoing first embodiment, an arcuate Groove 64 is formed through a predetermined angle on the circumference of the fixed shell 61a to receive therein a positioning pin 65 which is planted on the inner periphery of the twist ring 62.

Besides the arrangements just described, in order to detect the rotational angle of the movable shell 61b of the rear rigid rod section 61 when it is turned for a twist operation, a rotary inner sleeve 67 is fixedly connected to the inner periphery of the movable shell 61b by screws 66 at positions closer to the rear end of the movable shell 61b. The rotary inner sleeve 67 is extended through the fixed shell 61a and into the housing of the manipulating head assembly 57 at its rear end which is formed with a gear 67a around the circumference thereof. This gear 67a is meshed with an input gear 68a of an encoder 68, so that, as the movable shell 61b is turned about its axis, the inner sleeve 67 is turned therewith, permitting the encoder 68 to detect the rotational angle of the movable shell 61b. Accordingly, by connecting the encoder 68 to the angle detection circuit 47 in place of the potentiometer 39 of the foregoing first embodiment, ultrasound images can be similarly rotated according to a rotational angle of a twist operation.

In the above-described second embodiment, instead of rotating ultrasound images on display on a monitor screen by electronic image rotation responsive to a twist angle, arrangements may be made to turn the ultrasound transducer element itself through an angle commensurate with a twist operation.

Figure 8:
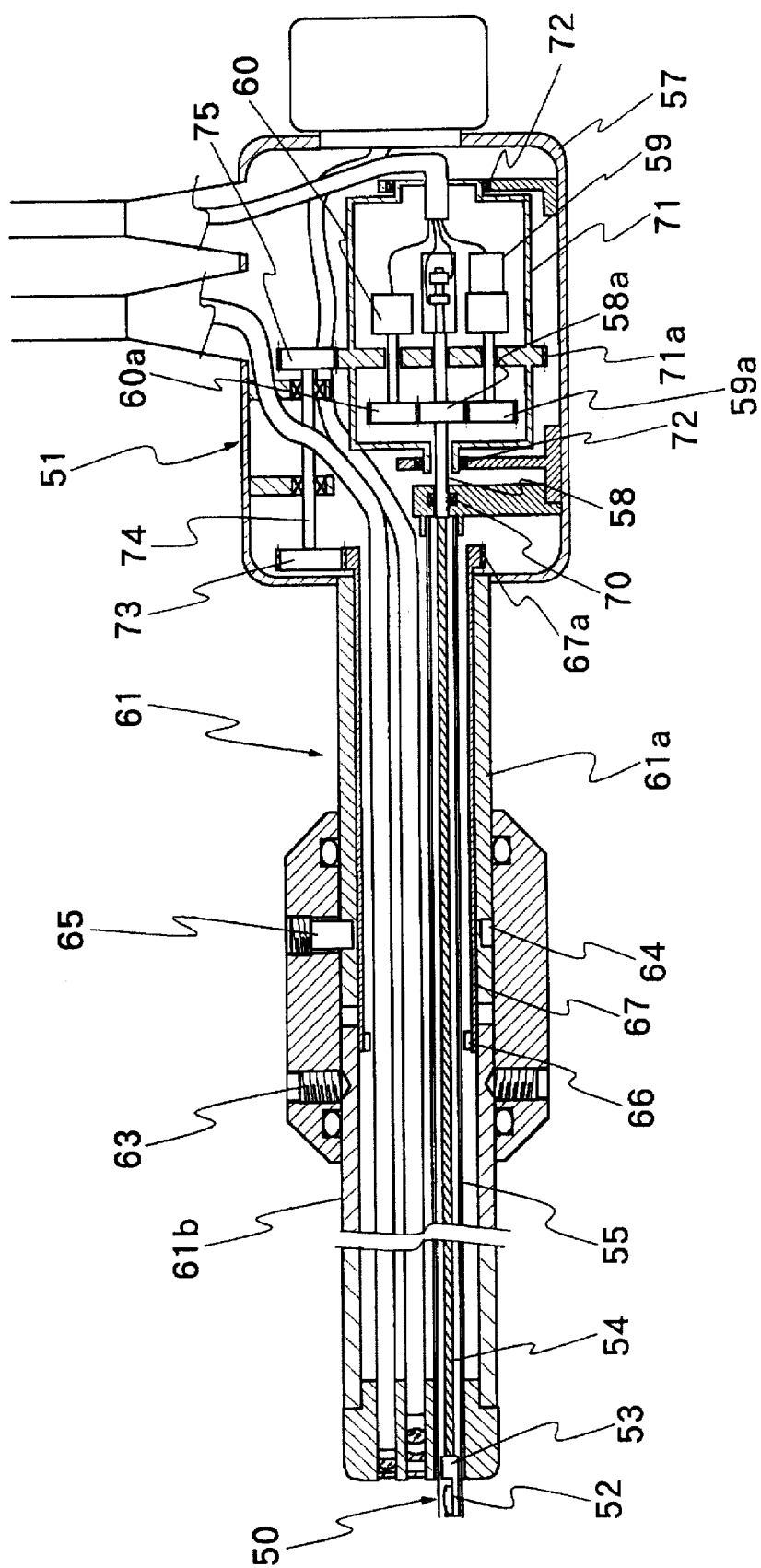
FIG. 8 is a schematic sectional view of an endoscopic insertion rod employed in a third embodiment of the invention.

Namely, shown in FIG. 8 is another embodiment of the invention, in which those component parts identical or common with the second embodiment of FIG. 7 are designated by similar reference numerals or characters. In this case, the rotational shaft 58 which is coupled with the flexible rotation transmission shaft 54 within the housing of the manipulating head assembly 57 is rotatably supported through a bearing 70. Further, the electric motor 59 and the encoder 60 which are coupled with the rotational shaft 58 are fixedly mounted within an inner rotary housing 71, which is rotatably supported through bearings 72. Therefore, rotation of the inner sleeve 67 is followed by the inner rotary housing 71 to turn the flexible shaft 54 within the flexible tube 55, thereby causing the ultrasound transducer element 52 to turn through an angle which corresponds to a twist angle.

To this end, the gear 67a at the rear end of the inner sleeve 67 is meshed with a first transmission gear 73 which is coupled with a rotational shaft 74. A second transmission gear 75 which is provided at the other end of the rotational shaft 74 is meshed with a gear 71a provided on the outer periphery of the rotary housing 71. In this instance, the gear 67a and the first transmission gear 73 are set at the same gear ratio as the second transmission gear 75 and the gear 71a, so that, at the time of a twist operation, the inner rotary housing 71 is turned through an angle commensurate with the angle of the twist operation. As a result, ultrasound observation images are constantly turned to match the endoscopic observation images in direction. Accordingly, the inner rotary sleeve 67 constitutes a rotational angle detection means serving to detect the rotational angle of movable sections of the endoscopic insertion rod 56 and to transmit the angle to the first transmission gear 73. On the other hand, the first transmission gear 73 and the second transmission gear 75, which is coupled with the first transmission gear 73 through the rotational shaft 74, constitute an ultrasound image rotating means serving to turn the ultrasound transducer element 52 through a detected angle, thereby rotating ultrasound images according to the angle of a twist operation.

As clear from the foregoing description, according to the present invention, as soon as fore movable sections of an endoscopic insertion rod is turned for a twist operation, the twist angle is detected to rotate ultrasound observation images according to the twist angle, thereby displaying ultrasound observation images on a monitor screen in a direction which matches endoscopic observation images, for improving accuracy of ultrasound examinations as conducted in combination with an endoscopic observation system.

What is claimed is:

1. An ultrasound endoscope system, comprising: an endoscope having a rotatable fore end section forward of a rigid non-rotatable section of an endoscopic insertion rod, said rotatable fore end section having an observation window and being rotatable about a longitudinal axis of said insertion rod to turn said endoscopic observation window at the distal end thereof;

an ultrasound probe to be introduced into a body cavity through said endoscopic insertion rod and into said fore end section, and having an ultrasound transducer at the distal end thereof for making radial scans independently of rotational movements of said movable fore end section of said endoscopic insertion rod:

an angle detection means for detecting a rotational angle of said rotatable fore end section of said endoscopic insertion rod with respect to said non-rotatable section when the rotatable fore end section is operated to turn view field of said endoscopic observation window and generating a signal representative of said angle; and an ultrasound image rotating means for turning a view field of a radial scan ultrasound image provided by said transducer on a monitor screen through an angle commensurate with a rotational angle of said rotatable fore end section of said endoscopic insertion rod on the basis of said signal from said angle detection means.

2. An ultrasound endoscope as defined in claim 1, wherein said angle detection means comprises an electrical circuit adapted to detect electrically said rotational angle of said rotatable fore section, and said ultrasound image rotating means comprises an electrical image rotation means adapted to shift an original scanning position of ultrasound image on display on said monitor screen in the rotational direction of said rotatable fore section of said endoscopic insertion rod.

3. An ultrasound endoscope as defined in claim 1, wherein said angle detection means comprises a cylindrical sleeve member connected to said rotatable fore section for rotation therewith, and said radial scan drive mechanism of said ultrasound probe is responsive to said signal to rotate said radial scan drive mechanism through an angle commensurate with said rotational angle of said rotatable fore section of said endoscopic insertion rod.

* * * * *